United States Patent
Plaza

(10) Patent No.: US 7,003,342 B2
(45) Date of Patent: Feb. 21, 2006

(54) CATHETER AND METHOD FOR MAPPING A PULMONARY VEIN

(75) Inventor: Claudio P. Plaza, Pasadena, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 10/452,185

(22) Filed: Jun. 2, 2003

(65) Prior Publication Data

US 2004/0242984 A1    Dec. 2, 2004

(51) Int. Cl.
A61B 5/042    (2006.01)

(52) U.S. Cl. .................................. 600/381; 600/374

(58) Field of Classification Search ................ 600/374, 600/381; 606/41; 607/122
See application file for complete search history.

(56) References Cited

U.S. PATENT DOCUMENTS

| | | |
|---|---|---|
| 4,522,212 A | 6/1985 | Gelinas et al. |
| 5,237,996 A | 8/1993 | Waldman et al. |
| 5,282,845 A | 2/1994 | Bush et al. |
| 5,327,889 A | 7/1994 | Imran |
| 5,391,199 A | 2/1995 | Ben-Haim |
| 5,411,025 A | 5/1995 | Webster, Jr. |
| 5,551,426 A | 9/1996 | Hummel et al. |
| 5,567,901 A | 10/1996 | Gibson et al. |
| 5,628,313 A | 5/1997 | Webster, Jr. |
| 5,683,384 A | 11/1997 | Gough et al. |
| 5,728,143 A | 3/1998 | Gough et al. |
| 5,741,214 A | 4/1998 | Ouchi et al. |
| 5,772,590 A | 6/1998 | Webster, Jr. |
| 5,782,239 A | 7/1998 | Webster, Jr. |
| 5,855,576 A | 1/1999 | LeVeen et al. |
| 5,908,446 A | 6/1999 | Imran |
| 5,935,102 A | 8/1999 | Bowden et al. |
| 5,938,694 A | 8/1999 | Jaraczewski et al. |
| 5,951,547 A | 9/1999 | Gough et al. |
| 6,053,937 A | 4/2000 | Burns et al. |
| 6,068,629 A | 5/2000 | Haissaguerre et al. |
| 6,071,280 A | 6/2000 | Edwards et al. |
| 6,216,044 B1 | 4/2001 | Kordis |
| 6,221,107 B1 | 4/2001 | Steiner |
| 6,231,570 B1 | 5/2001 | Tu et al. |

(Continued)

FOREIGN PATENT DOCUMENTS

EP        1297796 A      4/2003

(Continued)

OTHER PUBLICATIONS

European Search Report dated Aug. 23, 2004 for corresponding European Application No. 04253130.1, 4 pgs.

Primary Examiner—Lee S. Cohen
(74) Attorney, Agent, or Firm—Christie, Parker & Hale, LLP

(57) ABSTRACT

An improved catheter is provided that is particularly useful for mapping the pulmonary vein and other tubular regions of or near the heart. The catheter comprises an elongated catheter body having a proximal end, a distal end and at least one lumen extending longitudinally therethrough. A mapping assembly is mounted at the distal end of the catheter body and comprises a stem and at least two spines. The spines are moveable between a collapsed position, where each spine has a distal end attached to the stem, and a free proximal end positioned generally against the stem, and an expanded position, where the free proximal end of each spine extends outwardly from the stem. Each spine carries at least one electrode.

47 Claims, 6 Drawing Sheets

U.S. PATENT DOCUMENTS

| | | |
|---|---|---|
| 6,285,898 B1 | 9/2001 | Ben-Haim |
| 6,374,476 B1 | 4/2002 | Ponzi et al. |
| 6,389,311 B1 | 5/2002 | Whayne et al. |
| 6,402,746 B1 | 6/2002 | Whayne et al. |
| 6,574,492 B1 * | 6/2003 | Ben-Haim et al. .......... 600/374 |
| 6,669,693 B1 * | 12/2003 | Friedman ..................... 606/41 |
| 2001/0001819 A1 | 5/2001 | Lee et al. |
| 2002/0026188 A1 | 2/2002 | Balbierz et al. |
| 2002/0072742 A1 | 6/2002 | Schaefer et al. |
| 2002/0087157 A1 | 7/2002 | Sliwa, Jr. et al. |
| 2003/0050637 A1 | 3/2003 | Maguire et al. |
| 2003/0125614 A1 * | 7/2003 | Fuimaono et al. .......... 600/374 |

FOREIGN PATENT DOCUMENTS

| | | |
|---|---|---|
| WO | WO 96/05768 | 2/1996 |
| WO | WO 97/24981 | 7/1997 |
| WO | WO 97/24983 | 7/1997 |

* cited by examiner

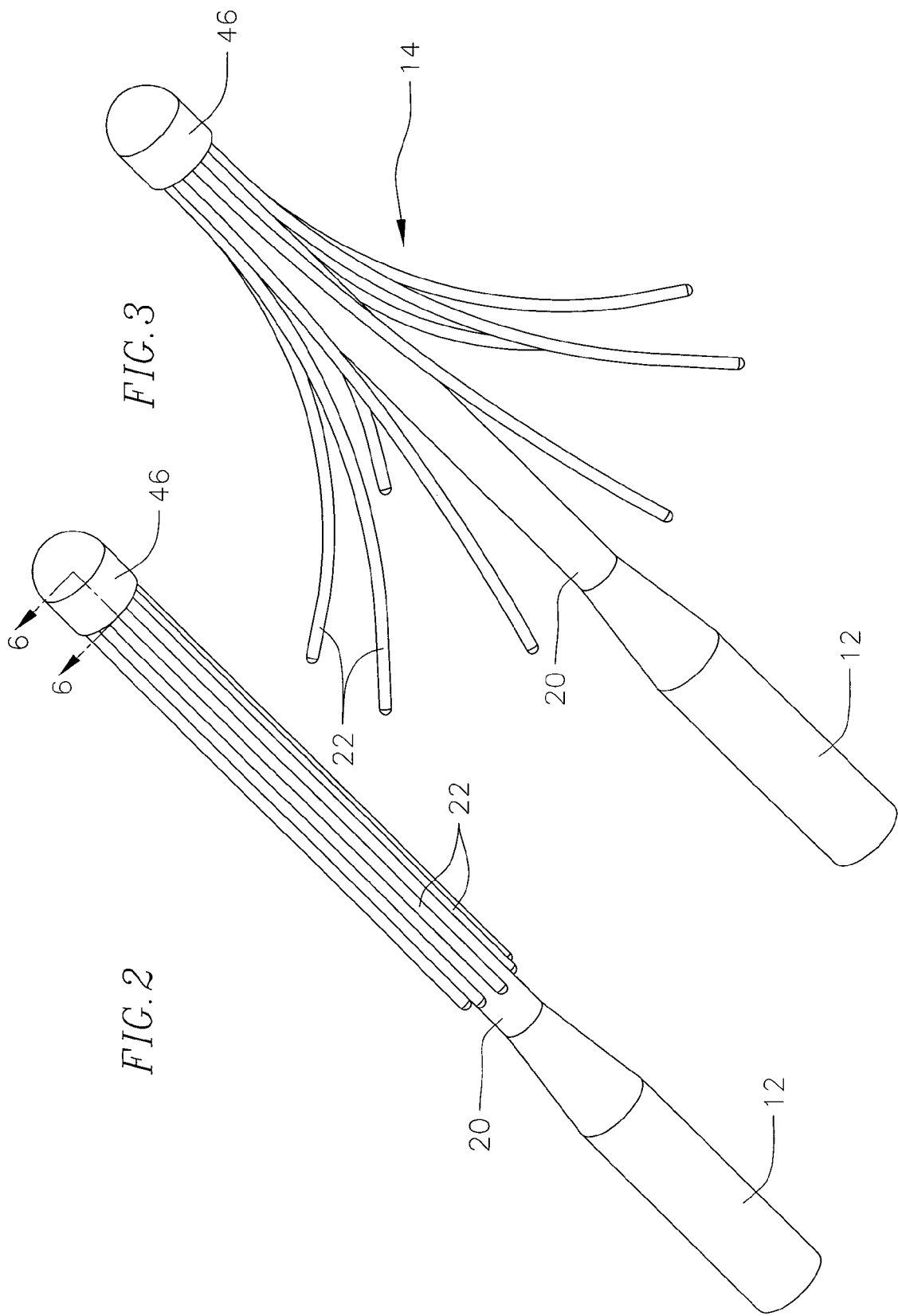

CATHETER AND METHOD FOR MAPPING A PULMONARY VEIN

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination. One proposed technique provides for measurement of the activity within a pulmonary vein, coronary sinus or other generally-tubular structure in or around the heart, where the activity is simultaneously measured at multiple points about the inner circumference of the structure.

A catheter for performing such a technique is described in allowed U.S. patent application Ser. No. 09/551,467, entitled "Catheter Having Mapping Assembly." The catheter includes a generally-circular electrode assembly at the distal end of the catheter. The generally-circular electrode assembly is introduced into the pulmonary vein so that the outer circumference of the electrode assembly is in contact with an inner circumference of the pulmonary vein. Using electrodes arranged on the electrode assembly, the electrical activity all around that circumference can be measured. This method is much more effective and accurate than separately measuring individual points along the circumference, for example, with a standard straight catheter carrying only a single mapping electrode or mapping electrode pair.

However, the pulmonary vein can be somewhat irregular in shape. In such circumstances, a generally-circular electrode assembly as described above may not make sufficient contact with the inner circumference of the pulmonary vein. Accordingly, a need exists for a catheter that can take into account irregularities in the pulmonary vein and contact a sufficient portion of an inner circumference of the pulmonary vein to map multiple points along the circumference simultaneously.

SUMMARY OF THE INVENTION

The present invention is directed to an improved catheter that is particularly useful for mapping a generally-tubular region of or near the heart, such as a pulmonary vein, the coronary sinus, the superior vena cava, or the pulmonary outflow tract, particularly where that region is somewhat irregularly shaped. In one embodiment, the invention is directed to a catheter comprising an elongated catheter body having a proximal end, a distal end and at least one lumen extending longitudinally therethrough. A mapping assembly is mounted at the distal end of the catheter body and comprises a stem and at least two spines. The spines are moveable between a collapsed position, where each spine has a distal end attached to the stem, and a free proximal end positioned generally against the stem, and an expanded position, where the free proximal end of each spine extends outwardly from the stem. Each spine carries at least one electrode.

The invention is also directed to a method for mapping a tubular region of or near the heart. The method comprises introducing the distal end of the catheter as described above into the tubular region. The mapping assembly is positioned so that at least one electrode from each spine is near or in contact with tissue within the tubular region. Electrical data received from the at least one electrode in contact with the tissue is recorded. Optionally, the mapping assembly is repositioned such that at least one electrode from each spine contacts a second different area of tissue within the tubular region, and electrical data from the second area of tissue is recorded.

DESCRIPTION OF THE DRAWINGS

These and other features and advantages of the present invention will be better understood by reference to the following detailed description when considered in conjunction with the accompanying drawings wherein:

FIG. 2 is a perspective view of a mapping assembly in the contracted position according to the invention.

FIG. 3 is a perspective view of a mapping assembly in the expanded position according to the invention.

DETAILED DESCRIPTION

Figure 1:
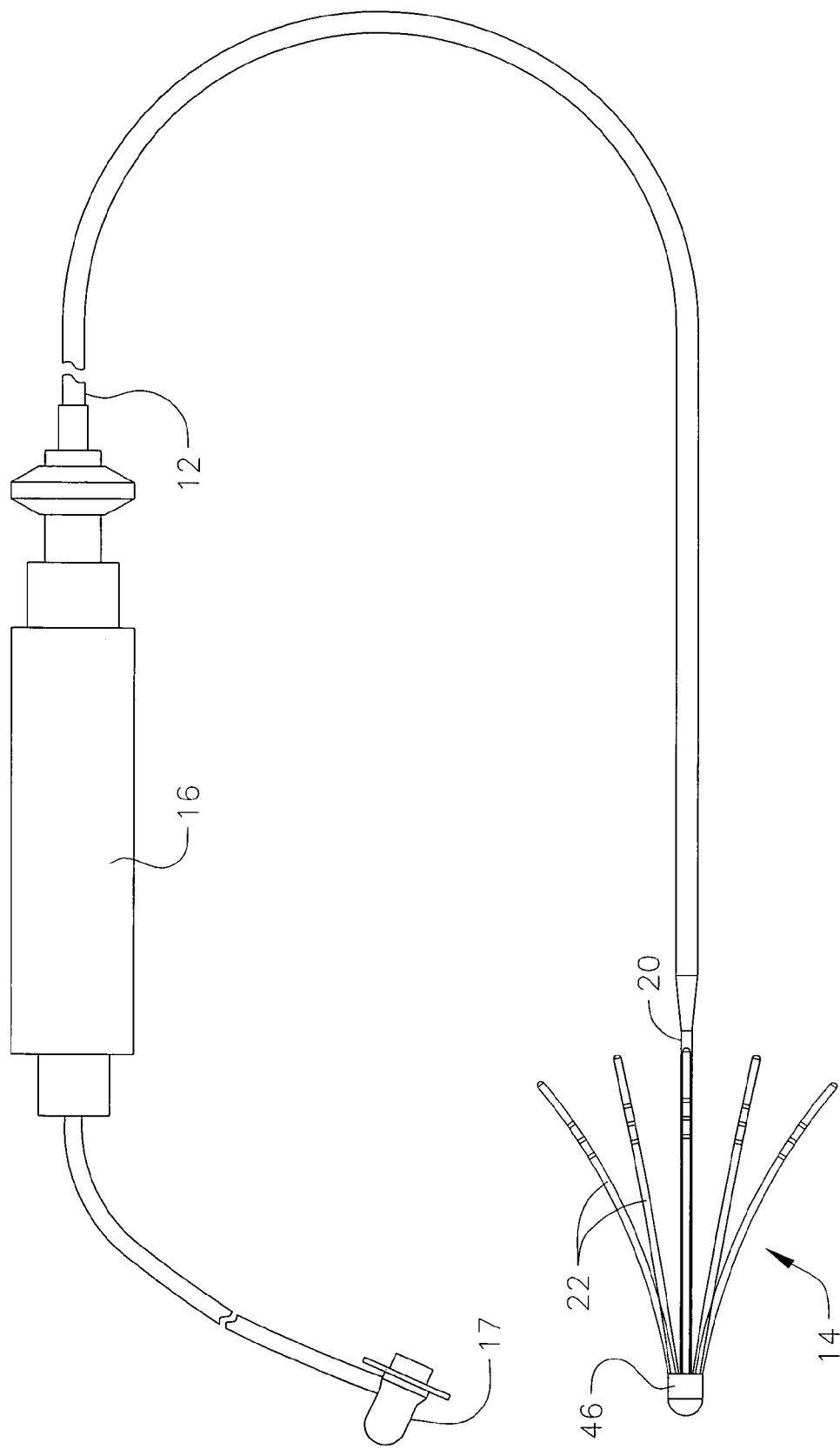
FIG. 1 is a side view of a catheter according to the invention.

As shown in FIG. 1, the catheter comprises an elongated catheter body 12 having proximal and distal ends, a mapping assembly 14 mounted at the distal end of the catheter body, and a handle 16 at the proximal end of the catheter body. The catheter body 12 comprises an elongated tubular construction having a single, axial or central lumen (not shown), but can optionally have multiple lumens if desired. The catheter body 12 is flexible, i.e., bendable, but substantially non-compressible along its length. The catheter body 12 can be of any suitable construction and made of any suitable material. A presently preferred construction comprises an outer wall made of polyurethane or PEBAX® (polyether block amide). The outer wall comprises an imbedded braided mesh of stainless steel or the like to increase torsional stiffness of the catheter body 12 so that, when the handle 16 is rotated, the distal end of the catheter body will rotate in a corresponding manner.

The outer diameter of the catheter body 12 is not critical, but is preferably no more than about 8 french, more preferably 7 french. Likewise the thickness of the outer wall is not critical, but is preferably thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

As shown in FIGS. 1 to 3, the mapping assembly 14 is mounted at the distal end of the catheter body 12 and comprises an elongated stem 20 and multiple spines 22 extending proximally from the stem. In the depicted embodiment, the stem 20 comprises a short tubing having an outer wall 21 and a proximal end mounted at the distal end of the catheter body 12. The stem is preferably made of a biocompatible plastic, such as polyurethane, PEBAX, or PEEK. In one embodiment, the short tubing is more rigid than the catheter body 12 so that the mapping assembly 14 remains generally straight. Alternatively, the short tubing of the stem 20 can have a flexibility similar to the catheter body 12, thereby permitting the mapping assembly to bend or deflect. The distal end of the catheter body 12 can also form the stem 20, in which case the catheter body 12 and stem 20 can be of a unitary construction comprising a single elongated tubing. The stem 20 preferably as an outer diameter less than the outer diameter of the catheter body 12 so that, when the mapping assembly is in a contracted arrangement, as described further below, the stem 20 and the collapsed spines 22 together have a diameter similar to the outer diameter of the catheter body.

Each spine 22 has a distal end attached to the stem 20, either directly or indirectly, and a free proximal end, i.e., the proximal end is not attached to any of the other spines, to the stem, to the catheter body, or to any other external structure that confines movement of the distal end. As is understood by those skilled in the art, the proximal end refers to the end closer to the user, and thus, in the present context, the end of the spine 22 that is closer to the handle 16.

The spines 22 are moveable between a contracted position, as shown in FIG. 2, and an expanded position, as shown in FIGS. 1 and 3. In the contracted position, the spines 22 are generally straight and are collapsed against the stem 20 so that they are generally parallel to the stem. In this collapsed position, the free proximal end is positioned generally against the stem, where a small space may or may not be provided between the free proximal end of the stem, and where another structure may or may not be provided between the stem and the free proximal end.

In the expanded position, the spines 22 are curved or bent so that their free proximal ends extend outward relative to the stem 20. In the depicted embodiment, the distal surfaces of the spines 22 face proximally to some extent, but each spine is curved outward to a sufficient extent to permit at least a portion of the distal surface of the tip electrode 30 on each spine to contact tissue within a tubular region.

In the depicted embodiment, the spines 22 are mounted at the distal end of the stem 20. Alternatively, the distal end of the stem 20 can extend beyond the distal ends of the spines 22 and optionally carry one or more measurement and/or treatment devices, such as an electrode, a temperature sensor, a balloon for anchoring the stem 20 in the pulmonary vein, or an irrigation mechanism.

FIGS. 1 to 3 show eight spines 22 extending from the stem 20, although the number of stems can be modified as desired. The mapping assembly 14 includes at least two spines 22, preferably four or more spines, still more preferably six or more spines, even more preferably eight or more spines.

The length of each spine is not critical. Preferably each spine has a total length (when straight) ranging from about 4 cm to about 16 cm, more preferably from about 6 cm to about 14 cm, still more preferably from about 9 cm to about 12 cm. Preferably all of the spines have the same length.

Figure 4:
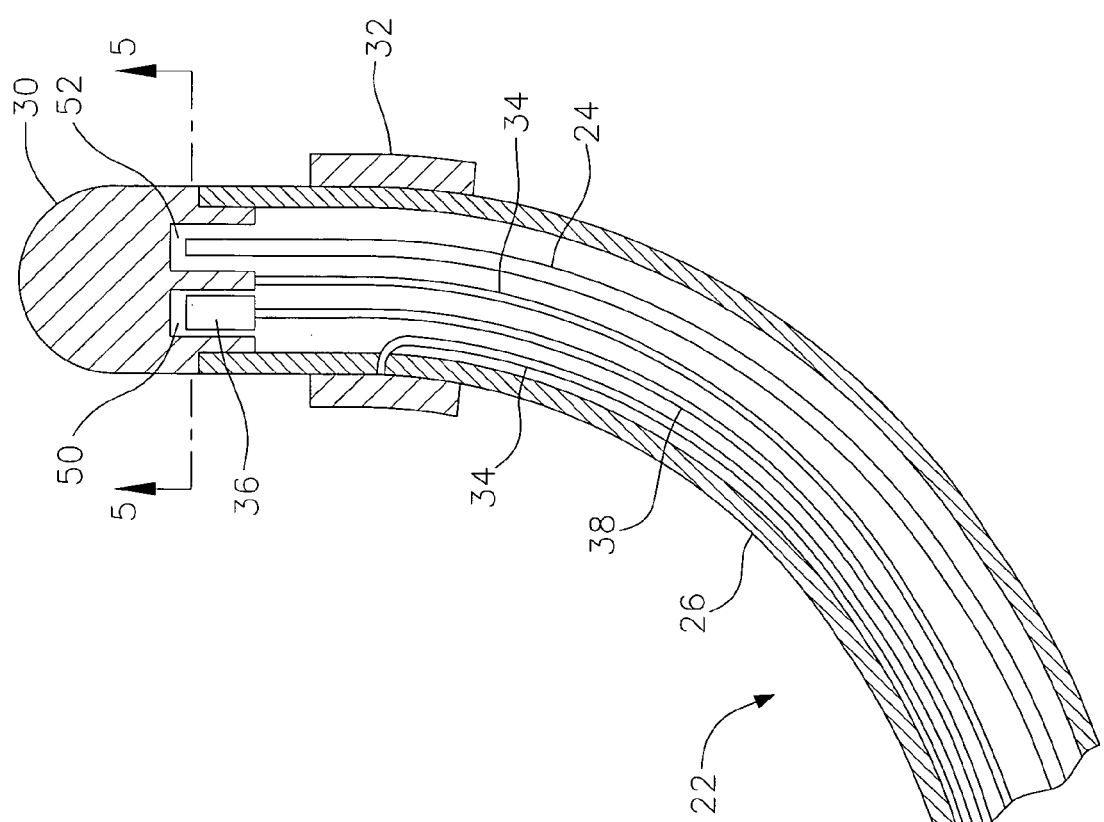
FIG. 4 is a side cross-sectional schematic view of one of the spines of the catheter of FIG. 1, taken from line 4—4 in FIG. 1.
Figure 5:
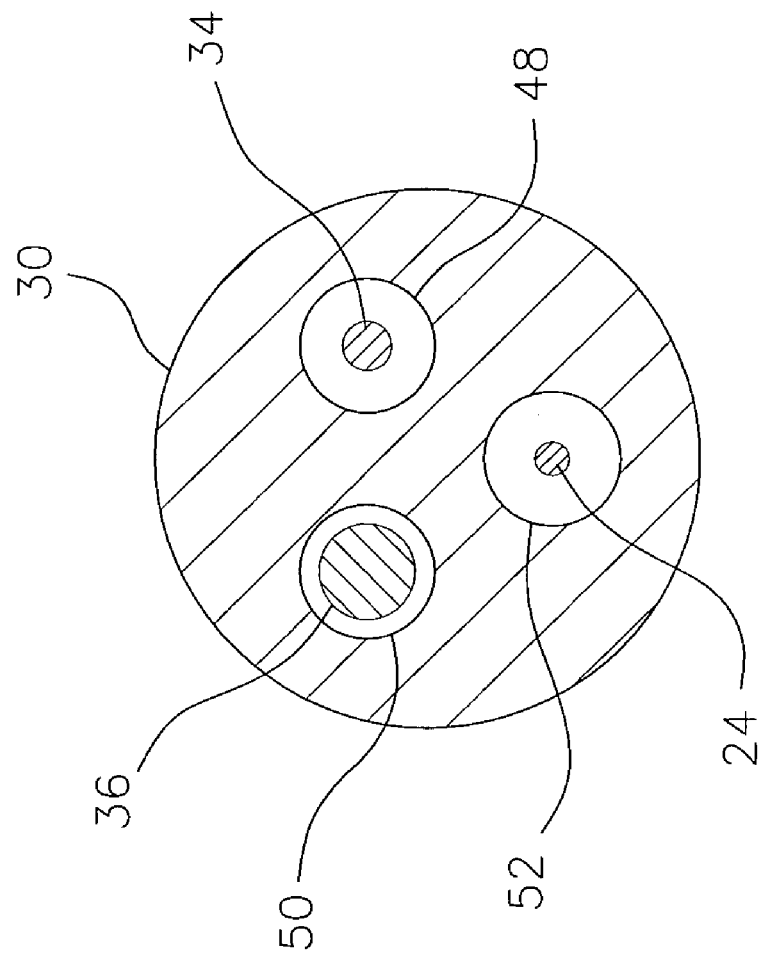
FIG. 5 is an end cross-sectional view of the tip electrode of the spine of FIG. 4, taken from line 5—5 in FIG. 4.

In the depicted embodiment, each spine 22 contains a support arm 24 and a non-conductive covering 26 in surrounding relation to the support arm 24, as best seen in FIGS. 4 and 5. In a preferred embodiment, the non-conductive covering 26 comprises a biocompatible plastic tubing, such as a polyurethane or polyimide tubing, having a closed proximal end and an open distal end.

The support arm 24 gives shape to the spine 22 when the spine is in the expanded position. In an exemplary embodiment, each support arm 24 is formed from a shape memory alloy of a nickel-titanium composition known as nitinol that forms the desired expanded shape when heated above a certain temperature. Type 55 nitinol, made of 55% by weight nickel and 45% titanium, and type 60 nitinol, made of 60% by weight nickel and 40% titanium, as well as various ternary and quaternary compositions of nitinol, can be used in the invention.

The heat may be achieved through resistive heating of the support arm 24 directly or by surrounding the support arm with a tubular heater. In the depicted embodiment, the heat is achieved through resistive heating by use of a first lead wire 28 connected to the distal end of the support arm and a second lead wire 29 connected to the proximal end of the support arm. The first and second lead wires 28 and 29 are connected to the support arm 24 by any suitable means, such as by soldering or welding. The proximal ends of the first and second lead wires 28 and 29 are connected to a suitable power supply, as is generally known in the art.

Each spine 22 carries one or more electrodes. In the depicted embodiment, a tip electrode 30 is mounted on the proximal end of each non-conductive covering 26 and a ring electrode 32 is mounted on each non-conductive covering 26, preferably on the proximal end of the non-conductive covering 26 adjacent the tip electrode. In this bipolar arrangement, the ring electrode 28 is used as a reference electrode. The distance between the tip electrode 30 and the ring electrode 32 preferably ranges from about 0.5 mm to about 2 mm. In an alternative bipolar arrangement (not shown), the tip electrode 30 is eliminated and at least two ring electrodes 32 are mounted on each non-conductive covering 26, preferably on the distal end of the non-conductive covering. Another alternative embodiment (not shown), is a unipolar arrangement, in which the tip electrode 30 is mounted on the distal end of each non-conductive covering 26, with one or more reference ring electrodes mounted on the distal end of the catheter body 12, or one or more reference electrodes attached outside the body of the patient (e.g., in the form of a patch). In an alternative unipolar arrangement, a ring electrode 32 mounted on each non-conductive covering 26, preferably on the distal end of the non-conductive covering 26, is used instead of a tip electrode 30. Two, three or more ring electrodes 32 can be included as desired. In yet another alternative, each spine 22 carries three, four or more electrode pairs for bipolar mapping along the length of the spine.

Each tip electrode 30 has an exposed length preferably ranging from about 0.5 mm to about 4 mm, more preferably from about 0.5 mm to about 2 mm, still more preferably about 1 mm. Each ring electrode 32 has a length preferably up to about 2 mm, more preferably from about 0.5 mm to about 1 mm.

Each tip electrode 30 and each ring electrode 32 is electrically connected to an electrode lead wire 34, which in turn is electrically connected to a connector 17. The connector 17 is connected to an appropriate mapping or monitoring system (not shown). Each electrode lead wire 34 extends from the connector 17, through the handle 16, through the catheter body 12, through the stem 20 and into the non-conductive covering 26 of its corresponding spine 22, where it is attached to its corresponding tip electrode 30 or ring electrode 32. Each lead wire 34, which includes a non-conductive coating over almost all of its length, is attached to its corresponding tip electrode 30 or ring electrode 32 by any suitable method.

A preferred method for attaching a lead wire 34 to a ring electrode 32 involves first making a small hole through an outer wall of the non-conductive covering 26. Such a hole can be created, for example, by inserting a needle through the non-conductive covering 26 and heating the needle sufficiently to form a permanent hole. The lead wire 34 is then drawn through the hole by using a microhook or the like. The end of the lead wire 34 is then stripped of any coating and welded to the underside of the ring electrode 32, which is then slid into position over the hole and fixed in place with polyurethane glue or the like. Alternatively, each ring electrode 32 may be formed by wrapping the lead wire 34 around the non-conductive covering 26 a number of times and stripping the lead wire of its own non-conductive coating on its outwardly facing surfaces. In such an instance, the lead wire 34 functions as a ring electrode.

In the depicted embodiment, each spine 22 also includes at least one location sensor 36. The location sensor 36 is mounted near the distal end of its corresponding spine 22. In the depicted embodiment, where each spine 22 comprises a tip electrode 30, each location sensor 36 is mounted such that the distal end of the location sensor 36 is secured within its corresponding tip electrode 30, while the proximal end of the location sensor 36 extends into the distal end of the non-conductive covering 26. Each location sensor 36 is used to determine the coordinates of its corresponding tip electrode 30 at each instant when the tip electrode is being used to collect an electrical mapping data point. As a result, both electrical and locational data can be obtained for each data point that is mapped. If the spine 22 carries at least one ring electrode 32 but does not include a tip electrode 30, the location sensor 36 is mounted near the distal end of the non-conductive covering 26, preferably as close to the distal end of the spine 22 as possible or concentric with the ring electrode 32.

Each location sensor 36 is connected to a corresponding sensor cable 38. Each sensor cable 38 extends through the non-conductive covering 26, catheter body 12 and handle 16 and out the proximal end of the handle within an umbilical cord (not shown) to a sensor control module (not shown) that houses a circuit board (not shown). Alternatively, the circuit board can be housed within the handle 16, for example, as described in U.S. Pat. No. 6,024,739, the disclosure of which is incorporated herein by reference. Each sensor cable 38 comprises multiple wires encased within a plastic covered sheath. In the sensor control module, the wires of the sensor cable 38 are connected to the circuit board. The circuit board amplifies the signal received from the corresponding location sensor 36 and transmits it to a computer in a form understandable by the computer by means of a sensor connector at the proximal end of the sensor control module. Also, where the catheter is designed for single use only, the circuit board preferably contains an EPROM chip that shuts down the circuit board approximately twenty-four hours after the catheter has been used. This prevents the catheter, or at least the location sensors 36, from being used twice.

Preferably each location sensor 36 is an electromagnetic location sensor. For example, each location sensor 36 may comprise a magnetic-field-responsive coil, as described in U.S. Pat. No. 5,391,199, or a plurality of such coils, as described in International Publication WO 96/05758. The plurality of coils enables the six-dimensional coordinates (i.e. the three positional and the three orientational coordinates) of the location sensor 36 to be determined. Alternatively, any suitable location sensor known in the art may be used, such as electrical, magnetic or acoustic sensors. Suitable location sensors for use with the present invention are also described, for example, in U.S. Pat. Nos. 5,558,091, 5,443,489, 5,480,422, 5,546,951, and 5,568,809, and International Publication Nos. WO 95/02995, WO 97/24983, and WO 98/29033, the disclosures of which are incorporated herein by reference. A particularly preferred location sensor 36 is a single axis sensor having a length ranging from about 3 mm to about 7 mm, preferably about 4 mm, such as that described in the U.S. patent application Ser. No. 09/882,125 filed Jun. 15, 2001, entitled "Position Sensor Having Core with High Permeability Material," the disclosure of which is incorporated herein by reference. Smaller sensors are particularly desirable for use in the present invention because of the need to keep the diameters of the spines 22 small enough so that they all fit within the lumen of a guiding sheath.

FIGS. 4 and 5 illustrate a suitable technique for mounting the electrode lead wire 34, the location sensor 36 and the support arm 24 to the tip electrode 30. The electrode lead wire 34 may be secured to the tip electrode 30 by drilling a first blind hole 48, preferably a bore hole, into the tip electrode 30, stripping the lead wire 34 of any coating and placing the lead wire 34 within the first blind hole 48 where it is electrically connected to the tip electrode 30 by a suitable means, such as by soldering or welding. The lead wire 34 may then be fixed in place, for example, by using a polyurethane glue or the like. The location sensor 36 may be similarly mounted within the tip electrode 30. For example, a second blind hole 50, preferably a bore hole, may be drilled into the tip electrode 30 such that the location sensor 36 may be inserted into the second blind hole 50 and affixed therein, for example, using a polyurethane glue or the like. The support arm 24 may also be similarly affixed to the tip electrode 30. For example, a third blind hole 52, preferably a bore hole, may be drilled into the tip electrode 30 such that the support arm 24 may be inserted into the third blind hole 52 and affixed therein, for example, using a polyurethane glue or the like. Alternatively, a single blind hole (not shown) in the proximal end of the tip electrode 30 can be used for mounting the location sensor 36 and support arm 24, and the distal end of the lead wire 34 can be wrapped around the outside proximal end of the tip electrode, which is not exposed and attached by solder, welding or any other suitable technique. Any other arrangement for mounting these components in the spine could also be used.

Figure 6:
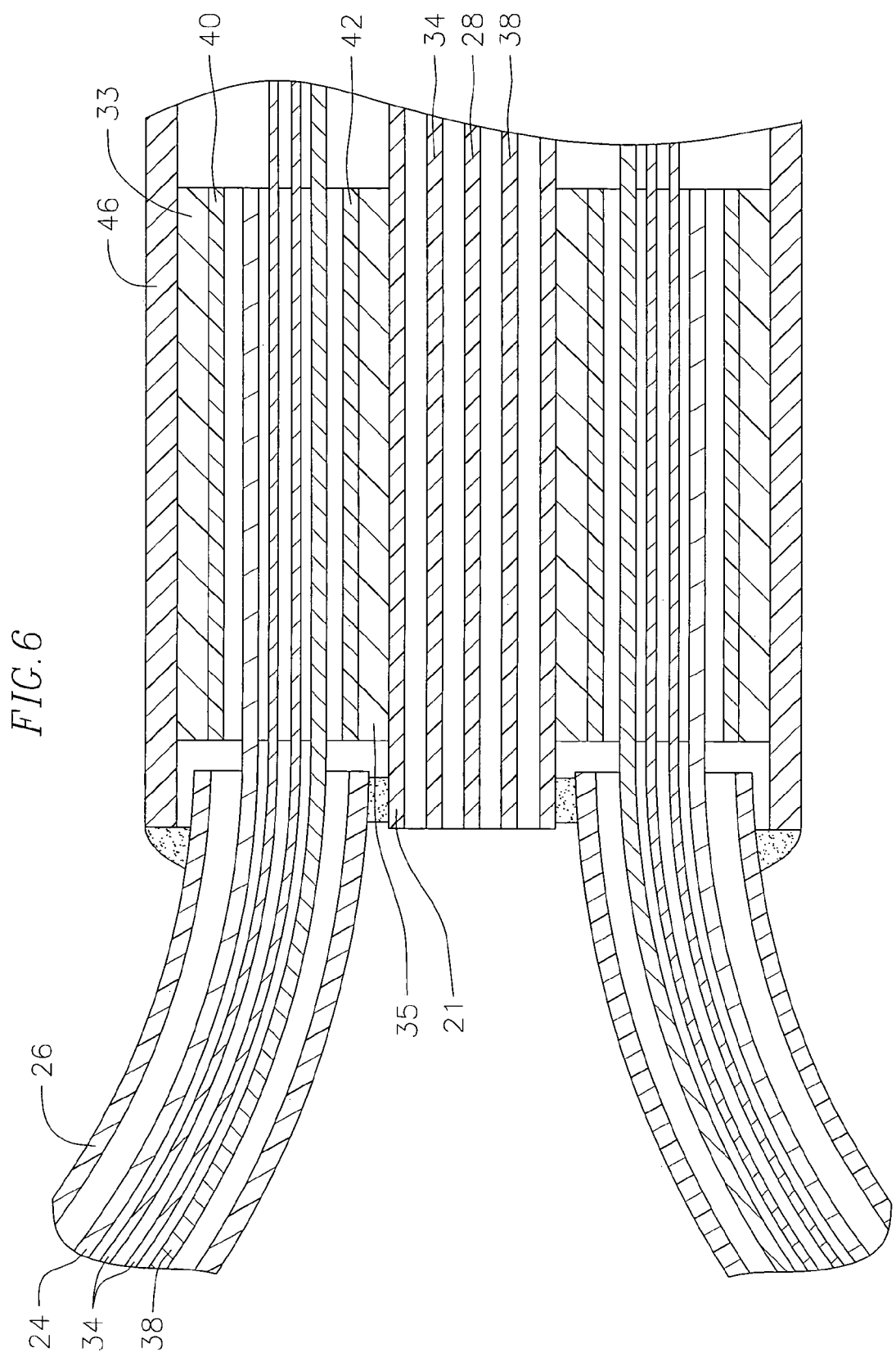
FIG. 6 is a side cross-sectional schematic view of a portion of the stem of the mapping assembly taken from line 6—6 in FIG. 2.
Figure 7:
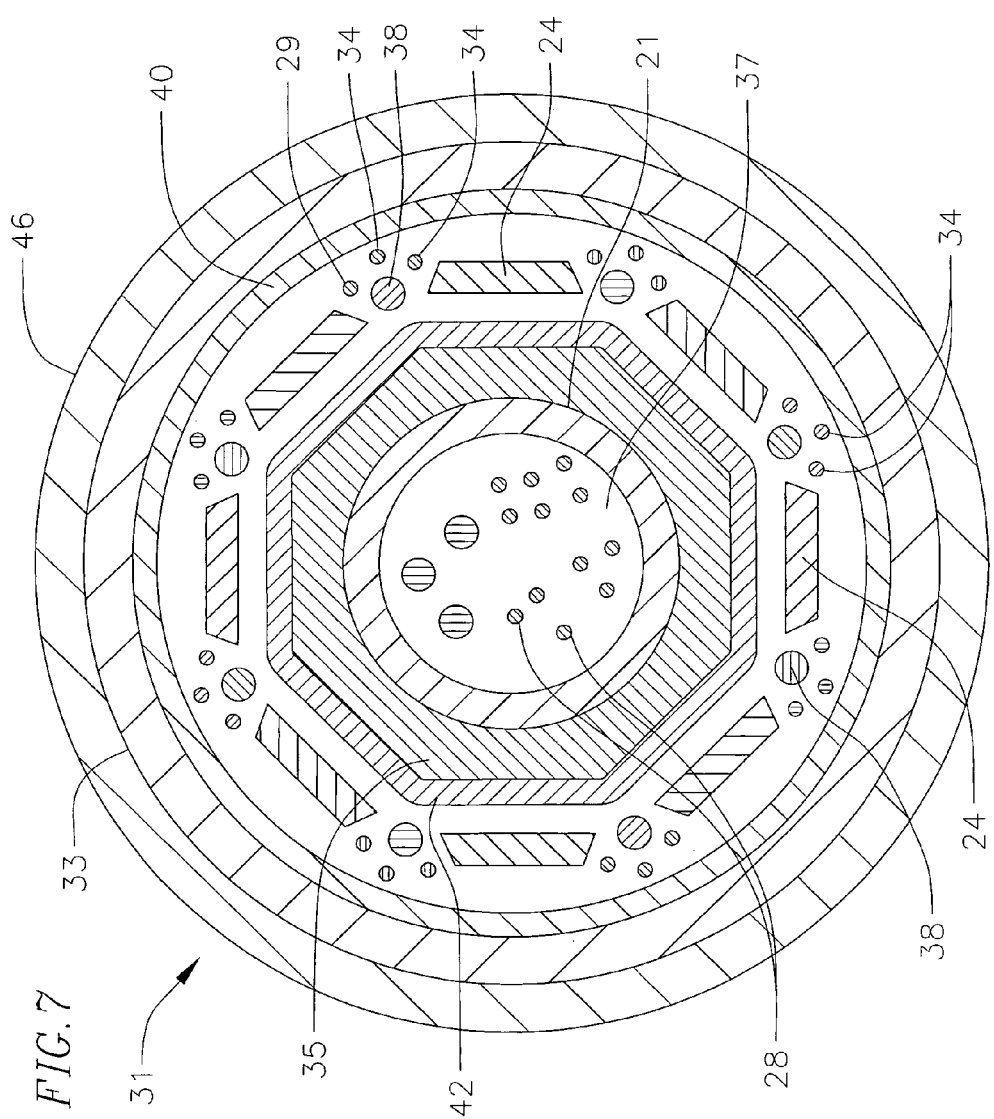
FIG. 7 is an end cross-sectional view of a portion of the stem taken from line 7—7 in FIG. 6.

A suitable construction of the distal end of the stem 20, having spines 22 mounted thereto, is depicted in FIGS. 6 and 7. For clarity, only two spines 22 are shown in FIG. 6. Mounted around the distal end of the stem 20 is a spine mounting assembly 31. The spine mounting assembly 31 comprises an outer mounting ring 33 and a mounting structure 35 provided coaxially within the outer mounting ring 33. The outer mounting ring 33 preferably comprises a metal material, such as stainless steel, more particularly stainless steel 303. Alternatively, the outer mounting ring 33 may comprise a plastic material.

The mounting structure 35 is multi-sided and comprises a metal material, such as stainless steel, more particularly stainless steel 303. The mounting structure 35 may also alternatively comprise a plastic material. The outer mounting ring 33 and the mounting structure 35 provide a channel 37 in which the distal end of each support arm 24 is mounted. Specifically, the distal end of each spine 22 is mounted to the stem 20 by removing a portion of the non-conductive covering 26 at the distal end of each spine 20, inserting the distal end of each support arm 24 into the channel 37 between the outer mounting ring 33 and the multi-sided mounting structure 35 and affixing each support arm 24 within the channel 38 by any suitable means, such as with a polyurethane glue or the like, so that the spine 22 is extending proximally from the outer mounting ring 33 and the mounting structure 35. The lead wires 34 and sensor cables 38 also extend through the channel 37 between the outer mounting ring 33 and the mounting structure 35.

In a preferred embodiment, each support arm 24 has a generally trapezoidally-shaped end cross section with curved sides. In such an arrangement, when each support arm 24 is inserted into the channel 37, a substantially flat surface of each support arm 24, preferably the base of the trapezoidally-shaped end cross section, is mounted against a substantially flat surface on the multi-sided mounting structure 35. Preferably the number of substantially flat outer surfaces on the multi-sided mounting structure 34 corresponds to the number of spines 14. In such an instance, the support arm 24 of each spine 22 may be mounted within the channel 37 and adjacent to its corresponding side on the multi-sided mounting structure 35 to enable the support arms 24, and thus the spines 22 to be equally spaced around the multi-sided mounting structure. The multi-sided mounting structure 35 is preferably approximately co-axial with the longitudinal axis of the stem 20 such that the spines 22 are equally spaced about the stem as well. Once each support arm 24 is properly positioned within the channel 37, each support arm 24 may be affixed within the channel 37 by any suitable means, such as by use of an adhesive, such as a polyurethane glue. Alternatively, the mounting structure 35 can have a round outer surface, although with such an embodiment more care needs to be taken if the support arms 24 are to be evenly spaced about the mounting structure.

In the depicted embodiment, a first non-conducting tube 40 is disposed between the outer mounting ring 33 and the support arms 24, and a second non-conducting tube 42 is disposed between the support arms 24 and the mounting structure 35. The non-conducting tubes 40 and 42, which may be polyimide tubes, ensure that each support arm 24 remains electrically isolated from the outer mounting ring 33 and mounting structure 35. If the outer mounting ring 33 and mounting structure 35 are made of plastic, the non-conducting tubes 40 and 42 can be eliminated if desired.

The stem 20 extends, preferably coaxially, through the mounting structure 35. The first and second lead wires 28 and 29, electrode lead wires 34 and sensor cables 38 bend around the distal end of the mounting structure 35 and stem 20 and proximally into the stem. For clarity, only some of the lead wires and sensor cables are shown around and within the stem in FIGS. 6 and 7. From the stem 20, the first and second lead wires 28 and 29, electrode lead wires 34 and sensor cables 38 extend through the catheter body 12 and into the handle 16, and optionally out through the proximal end of they handle, where they are attached to appropriate connectors (not shown).

A plastic cap 46 is mounted on the distal end of the stem 20 in surrounding relation to the spine mounting assembly 31 with the sides of the plastic cap being wrapped around the outer mounting ring 33. The plastic cap 46 may be attached by a variety of methods, such as by use of an adhesive, such as a polyurethane glue. The plastic cap 46 can be replaced with a plastic ring (not shown), and polyurethane glue or the like can be used to form a ball-shaped distal tip at the distal end of the stem 20 that serves as an a traumatic tip and also serves to seal in the first and second lead wires 28 and 29, electrode lead wires 34 and sensor cables 38 and close the distal end of the stem 20.

In another embodiment, a plastic ring (not shown) is used, and an irrigation or guidewire tube (not shown) is mounted coaxially within the stem 20 so that irrigation fluid can be passed through the irrigation tube or the catheter can be guided over the guidewire tube. Such an arrangement is described in U.S. patent application Ser. No. 10/231,857, entitled "Catheter and Method for Mapping Purkinje Fibers," the disclosure of which is incorporated herein by reference. Other arrangements for mounting the distal ends of the spines 22 to the stem 20 are within the scope of the invention.

To use the catheter of the invention, a cardiologist or electrophysiologist introduces a guiding sheath and a dilator into the patient, as is generally known in the art, so that the distal ends of the sheath and dilator are in the region of the heart to be mapped. Thereafter, the dilator is removed from the guiding sheath, and the catheter is introduced into the patient through the guiding sheath. To insert the catheter into the guiding sheath, the mapping assembly 14 must be in its collapsed arrangement, wherein each spine 22 is disposed generally along the longitudinal axis of the stem 20. A suitable guiding sheath for use in connection with the catheter is the PREFACE™ Braided Guiding Sheath (commercially available from Biosense Webster, Inc., Diamond Bar, Calif.). Such a guiding sheath has sufficient strength to hold each support arm 24 in the collapsed arrangement, such that the spines 22 and also the entire remainder of the catheter can travel within the guiding sheath, from an insertion point in the patient, through a vein or artery and to a desired location in the heart.

Once the distal end of the catheter has reached the desired location, such as a position within a pulmonary vein or other tubular region of or near the heart, relative longitudinal movement between the catheter and the guiding sheath is provided to allow the mapping assembly 14 to protrude from the guiding sheath. The spines 22 are then expanded by resistively heating the support arms 24 so that the proximal ends of the spines 22 extend outward from the stem 20 to contact a circumference of tissue within the pulmonary vein. Alternatively, the guiding sheath may be moved away from the mapping assembly 14 within the heart and then the stem 20 and spines 22 can then be advanced into the pulmonary vein or other tubular region by pushing the catheter distally.

In the expanded arrangement, at least one electrode from each spine 14 can be placed near or into contact with tissue within the pulmonary vein or other tubular region such that electrical, locational and/or mechanical information can be obtained from the contacted heart tissue. The proximally- and outwardly-extending shape of the spines is advantageous in that they have a tendency to exert an outward force on the tissue once they are expanded and confined within a tubular region. This force helps to assure that all of the spines are in contact with the tissue. Moreover, this design permits the spines to contact an inner circumference within a tubular region even if the inner circumference is somewhat irregularly shaped because each spine will tend to be expanded or compressed within the tubular region to the extent permitted by the tissue arrangement. Accordingly, irregularly-shaped tubular regions can be mapped more accurately than with a circular electrode assembly. This design also permits tubular regions of varying sizes to be mapped with a single size mapping assembly. Although circular electrode assemblies can be adjusted within the body to permit tubular regions of varying sizes to be mapped with a single size mapping assembly, the inventive mapping assembly offers the further advantage that such adjustment is easier to accomplish because, when the spines expand, they more readily conform to the size and shape of the tissue.

If the spines 20 all have the same length, the tip electrodes 30 will generally tend to contact a circumference within the tubular region. After the tissue near or in contact with the electrodes has been mapped, the catheter can be advanced distally to map a new area of tissue. This process can be repeated as desired. Further, if electrodes are mounted along the length of the spines, such electrodes can be used to map the ostium.

After mapping is completed, the heat is removed from the support arm, thereby causing the support arm to return to its collapsed potion. The catheter is then moved proximally relative to the guiding sheath to retract the mapping assembly within the sheath. Alternatively, the guiding sheath can be moved distally relative to the catheter. Using the inventive catheter having multiple spines, each having electrical and mechanical mapping and locational sensing capabilities, the cardiologist can map local activation time and obtain voltage maps. The cardiologist can also determine those locations in the pulmonary vein or other tubular region having no mechanical activity by monitoring whether the position of the location sensor changes over a complete cardiac cycle. This information can guide the cardiologist in providing therapy to the patient. For example, where the cardiologist finds regions of the heart that do not have mechanical activity, he or she can revascularize those regions using known techniques, such as gene therapy or transmyocardial revascularization. The inventive catheter allows the cardiologist to map the heart more quickly than traditional catheters by measuring multiple points of data at a time.

Other arrangements for expansion and contraction of the spines are considered within the scope of the invention. For example, the support arm can comprise a metal or plastic material that has shape memory, such as nitinol, so that the support arm forms an initial shape (its outwardly-curved shape) when no external forces are applied, forms a deflected (in this case, straight) shape when an external force is applied, and returns to its initial shape when the external force is released. With such a design, wires or the like can be attached to the spine to return them to the deflected (straight) position so that the guiding sheath can be moved back over the mapping assembly. The use of the support arm is not critical so long as the spine can be moved back and forth from its expanded and contracted positions.

If desired, the catheter may include a steering mechanism for deflection of the distal end of the catheter body 12. With such a design, the distal end of the catheter body 12 preferably comprises a short length of tubing, e.g., 2 to 4 inches in length, that is more flexible than the remainder of the catheter body 12. A suitable steering mechanism comprises a puller wire (not shown) that extends from a proximal end in the handle 16, through the catheter body 12 and into an off-axis lumen in the short length of tubing. Within the catheter body 12, the puller wire extends through a closely wound coil that is bendable but substantially non-compressible. The coil is fixed near the proximal and distal ends of the catheter body 12 and prevents deflection of the catheter body 12. The distal end of the puller wire is anchored at the distal end of the short length of tubing in the off axis lumen. The proximal end of the puller wire is anchored to a movable member in the handle 16 that can be moved relative to the catheter body 12. Proximal movement of the movable member relative to the catheter body 12 results in deflection of the short length of tubing. An example of such a steering mechanism and construction is described in more detail in U.S. Pat. No. 6,064,905, the disclosure of which is incorporated herein by reference. When incorporating a steering mechanism into the inventive catheter, it may be desirable to include a location sensor at the distal end of the catheter body 12. As would be recognized by one skilled in the art, if a steering mechanism is not including, the handle 16 can be eliminated, although it is desirable to maintain the handle for ease of use by the cardiologist.

The preceding description has been presented with references to presently preferred embodiments of the invention. Persons skilled in the art and technology to which this invention pertains will appreciate that alterations and changes in the described structures and methods can be practiced without meaningfully departing from the principle, spirit and scope of this invention. Accordingly, the foregoing description should not be read as pertaining only to the precise structures and methods described and shown in the accompanying drawings, but rather should be read as consistent with and as support for the following claims, which are to have their fullest and fairest scope.

What is claimed is:

1. A catheter comprising:
an elongated catheter body having a proximal end, a distal end and at least one lumen extending longitudinally therethrough;
a mapping assembly mounted at the distal end of the catheter body and comprising a stem and at least two spines, the stem comprising a short tubing having an outer wall and a proximal end mounted at the distal end of the catheter body, wherein the short tubing of the stem is more rigid than the catheter body, wherein each spine has a distal end attached to the stem and a free proximal end positioned generally against the stem, and wherein each spine carries at least one electrode, the spines being moveable between a collapsed position and an expanded position where the free proximal end of each spine extends outwardly from the stem.

2. The catheter according to claim 1, wherein the at least one electrode carried by each spine comprises a tip electrode mounted at the proximal end of the spine.

3. The catheter of claim 2, wherein each tip electrode has an exposed length ranging from about 0.5 mm to about 4 mm.

4. The catheter of claim 2, wherein each tip electrode has an exposed length ranging from about 0.5 mm to about 2 mm.

5. The catheter of claim 2, wherein each tip electrode has an exposed length of about 1 mm.

6. The catheter according to claim 1, wherein each spine carries at least two electrodes.

7. The catheter according to claim 1, wherein the spines are evenly-spaced around the stem.

8. The catheter according to claim 1, wherein the mapping assembly comprises at least four spines.

9. The catheter according to claim 1, wherein the mapping assembly comprises at least six spines.

10. The catheter according to claim 1, wherein the mapping assembly comprises at least eight spines.

11. The catheter according to claim 1, wherein the at least two spines are the same length.

12. The catheter of claim 1, wherein each spine carries at least four electrodes.

13. The catheter of claim 1, wherein each spine has a length ranging from about 4 cm to about 16 cm.

14. The catheter of claim 1, wherein each spine has a length ranging from about 6 cm to about 14 cm.

15. The catheter of claim 1, wherein each spine has a length ranging from about 9 cm to about 12 cm.

16. The catheter of claim 1, wherein each spine comprises a non-conductive covering having a support arm that has shape memory disposed therein.

17. The catheter of claim 16, wherein each support arm comprises nitinol.

18. The catheter of claim 16, further comprising a spine mounting assembly mounted around the distal end of the stem, the spine mounting assembly comprising:
  an outer mounting ring; and
  a mounting structure provided coaxially within the outer mounting ring;
  wherein the outer mounting ring and the mounting structure provide a channel in which the distal end of each support arm is mounted.

19. The catheter of claim 18, wherein the stem extends coaxially through the mounting structure.

20. The catheter of claim 1, wherein the spines are mounted at the distal end of the stem.

21. The catheter of claim 1, wherein the distal end of the stem extends beyond the distal ends of the spines.

22. The catheter of claim 21, further comprising at least one measurement device carried by the distal end of the stem.

23. The catheter of claim 21, further comprising at least one treatment device carried by the distal end of the stem.

24. The catheter of claim 1, wherein the at least one electrode carried by each spine comprises a tip electrode and at least one ring electrode.

25. The catheter of claim 24, wherein the distance between the tip electrode and the at least one ring electrode ranges from about 0.5 mm to about 2 mm.

26. The catheter of claim 1, wherein the at least one electrode carried by each spine comprises at least one ring electrode.

27. The catheter of claim 1, wherein the at least one electrode carried by each spine comprises a plurality of electrode pairs disposed along the length of the spine.

28. The catheter of claim 1, each spine further comprising at least one location sensor.

29. The catheter of claim 28, wherein each location sensor is an electromagnetic location sensor.

30. The catheter of claim 28, wherein each location sensor is a single axis sensor having a length ranging from about 3 mm to about 7 mm.

31. The catheter of claim 28, wherein each location sensor is a single axis sensor having a length of about 4 mm.

32. A method for mapping a tubular region of or near the heart comprising:
  introducing the distal end of the catheter of claim 1 into the tubular region;
  positioning the mapping assembly so that at least one electrode from each spine is near or in contact with tissue within the tubular region;
  recording electrical data received from the at least one electrode in contact with tissue.

33. The method of claim 32, further comprising repositioned the mapping assembly such that at least one electrode from each spine contacts a second different area of tissue within the tubular region; and
  recording electrical data from the second area of tissue.

34. The method of claim 32, wherein the distal end of the catheter is introduced through a guiding sheath having a distal end positioned in or near the heart so that the spines of the mapping assembly are covered by the guiding sheath during introduction.

35. The method of claim 32, comprising positioning the mapping assembly so that at least one electrode from each spine is in contact with tissue within the tubular region.

36. A method for mapping a tubular region of or near the heart comprising:
  introducing into the tubular region the distal end of a catheter comprising:
    an elongated catheter body having a proximal end, a distal end and at least one lumen extending longitudinally therethrough,
    a mapping assembly mounted at the distal end of the catheter body and comprising a stem and at least two spines moveable between a collapsed position, where each spine has a distal end attached to the stem and a free proximal end positioned generally against the stem, and an expanded position, where the free proximal end of each spine extends outwardly from the stem, and wherein each spine carries at least one electrode;
  positioning the mapping assembly so that at least electrode from each spine is near or in contact with tissue within the tubular region, wherein the positioning step comprises resistively heating a support member within each spine; and
  recording electrical data received from the at least one electrode in contact with the tissue.

37. The method of claim 32, wherein the tubular region is selected from the group consisting of the pulmonary vein, the coronary sinus, the superior vena cava, and the pulmonary outflow tract.

38. The method of claim 32, wherein the tubular region is the pulmonary vein.

39. The method of claim 32, wherein each spine carries a tip electrode mounted at the distal end of the spine.

40. The method of claim 32, wherein the catheter comprises at least eight spines.

41. The method of claim 32, wherein each spine has a length ranging from about 4 cm to about 16 cm.

42. The method of claim 32, wherein each spine has a length ranging from about 6 cm to about 14 cm.

43. The method of claim 32, wherein each spine has a length ranging from about 9 cm to about 12 cm.

44. The method of claim 32, wherein each spine comprises a non-conductive covering having a support arm that has shape memory disposed therein.

45. The method of claim 44, wherein each support arm comprises nitinol.

46. A catheter comprising:
  an elongated catheter body having a proximal end, a distal end and at least one lumen extending longitudinally therethrough;
  a mapping assembly mounted at the distal end of the catheter body and comprising a stem and at least two spines moveable between a collapsed position, where each spine has a distal end attached to the stem and a free proximal end positioned generally against the stem, and an expanded position, where the free proximal end of each spine extends outwardly from the stem, wherein each spine carries at least one electrode, and wherein the stem has an outer diameter less than an outer diameter of the catheter body, such that when the mapping assembly is in the collapsed position, the stem and the spines together have a diameter similar to the outer diameter of the catheter body.

47. A catheter comprising
  an elongated catheter body having a proximal end, a distal end and at least one lumen extending longitudinally therethrough;
  a mapping assembly mounted at the distal end of the catheter body and comprising a stem and at least two spines moveable between a collapsed position, where each spine has a distal end attached to the stem and a free proximal end positioned generally against the stem, and an expanded position, where the free proximal end of each spine extends outwardly from the stem, and wherein each spine carries at least one electrode, each spine comprising a non-conductive covering having a support arm that has shape memory disposed therein, the catheter further comprising a spine mounting assembly mounted around the distal end of the stem, the spine mounting assembly comprising an outer mounting ring;

a mounting structure provided coaxially within the outer mounting ring;

a first non-conducting tube disposed between the outer mounting ring and the support arms; and a second non-conducting tube disposed between the support arms and the mounting structure, wherein the outer mounting ring and the mounted structure provide a channel in which the distal end of each support arm is mounted.

* * * * *

UNITED STATES PATENT AND TRADEMARK OFFICE
CERTIFICATE OF CORRECTION

PATENT NO.         : 7,003,342 B2
APPLICATION NO. : 10/452185
DATED              : February 21, 2006
INVENTOR(S)       : Plaza It is certified that error appears in the above-identified patent and that said Letters Patent is hereby corrected as shown below:

In the Claims

| | |
|---|---|
| Column 11, lines 51-52, Claim 33 | Delete "repositioned", Insert --repositioning-- |
| Column 12, line 12, Claim 36 | After "that at least", Insert --one-- |
| Column 14, line 5, Claim 47 | Delete "mounted", Insert --mounting-- |

Signed and Sealed this

Twenty-first Day of November, 2006

JON W. DUDAS
*Director of the United States Patent and Trademark Office*